United States Patent [19]

Makofski et al.

[11] Patent Number: 4,610,249

[45] Date of Patent: Sep. 9, 1986

[54] MEANS AND METHOD FOR THE NONINVASIVE FRAGMENTATION OF BODY CONCRETIONS

[75] Inventors: Robert A. Makofski, Catonsville; Joe T. Massey, Bethesda; F. Fausten Mark, Silver Spring; Francis B. Weiskopf, Jr., Catonsville; William H. Guier, Pasadena; Patrick C. Walsh, Hunt Valley; Fray F. Marshall, Ruxton, all of Md.

[73] Assignee: The Johns Hopkins University, Baltimore, Md.

[21] Appl. No.: 608,114

[22] Filed: May 8, 1984

[51] Int. Cl.⁴ ............................................. A61B 17/22
[52] U.S. Cl. ...................................................... 128/328
[58] Field of Search ................... 128/24 R, 328, 804, 128/24 A

[56] References Cited

U.S. PATENT DOCUMENTS 3,942,531 3/1976 Hoff ..................................... 128/328
4,311,147 1/1982 Hausler .............................. 128/328

FOREIGN PATENT DOCUMENTS 3146626 6/1983 Fed. Rep. of Germany ...... 128/328

OTHER PUBLICATIONS

Chaussy, Extracorporeal Shock Wave Lithotripsy, 1980, pp. 1–111, "Berührungsfreie Nierensteinzertrümmerung Durch Extrakorporal Erzeugte, Fokussierte Stosswellen", beiträge Zur Urologie, vol. 2 (Krager, Basel 1980) ISBN 3-8055-1901-X.

Primary Examiner—Clifford D. Crowder
Attorney, Agent, or Firm—Robert E. Archibald; Carl I. Brundidge

[57] ABSTRACT

Apparatus and method for noninvasive fragmentation of body concretions. The apparatus has an integral unit including an ultrasonic locating transducer and positioning structure. The concretion is localized with ultrasonics and then shattered upon generation of a shockwave, using a relfector with first and second foci. A spark gap at the first focus generates the shockwave which propagates to the second focus coincident with the concretion. The ultrasonic tranducer is positioned so that an axis of the transducer is coincident with a straight line passing through the first and second foci.

14 Claims, 4 Drawing Figures

MEANS AND METHOD FOR THE NONINVASIVE FRAGMENTATION OF BODY CONCRETIONS

BACKGROUND OF THE INVENTION

This invention relates generally to a device for the noninvasive fragmentation of body concretions and more particularly to a device with an integral ultrasonic locating and positioning means whereby the concretion is localized with ultrasonics and the device is positioned in response to ultrasonicly derived information.

The formation of body concretions is a fairly common occurrence in humans. For example, it is estimated that one of every ten American males and one of every forty American females will be treated for kidney stones, one of the most common body concretions, during their lifetime. The occurrence of kidney stones is usually debilitating to the patient and causes a significant loss of productive labor to industry. In many cases, treatment requires major and often repeated surgery. Many attempts have been made to develop a simple and effective noninvasive treatment of kidney stones. One such method involves chemical dissolution of the stone, however, most of these attempts have been unsuccessful and impractical because of the slowness of the dissolution process.

Another method involves the direct contact of the concretion by the energy source. As such the procedures of this method are either transurethral or surgical. Two of the most common procedures are the electrohydraulic shockwave and the ultrasonic lithotripter. The electrohydraulic shockwave is generated via two well-isolated, high voltage leads which are carried by a common cystoscope to the stone and a high capacity condenser is discharged via the probe causing a spark to jump between two poles. This sparking causes a hydrodynamic wave which destroys the concretion upon contact. The ultrasonic lithotripter device produces ultrasonic waves which are carried by a hollow steel probe to the concretion. These two methods are generally limited to treatment of bladder stones.

The advent of high-speed physics and the development of a method of generating shockwaves by an underwater spark gap led to a method of noninvasive fragmentation of body concretions. One such device for the noninvasive fragmentation of kidney stones includes a large bath in which the patient is immersed, crossed X-ray beams for the localization of the stone and an underwater spark gap for the generation of high energy shockwaves which are focused at the kidney stone.

As can be appreciated a system such as described above has many disadvantages. The large space required for the bath and the X-ray system as well as the electronics for the generation of the underwater spark gap is a major detriment. Another detriment is that it requires multiple shockwaves to fragment the stone to particles that will pass through the urinary system and the repeated positioning of the spark gap apparatus requires multiple X-rays which are very detrimental to the patient.

It is therefore one object of this invention to provide a method and apparatus for the noninvasive fragmentation of body concretions that is simple, small in size, effective and inexpensive for the patient.

It is another object of this invention to provide a method and apparatus for the noninvasive fragmentation of body concretions that does not require multiple X-rays of the patient.

It is a further object of this invention to provide method and apparatus for the noninvasive fragmentation of body concretions that does not require the immersion of the patient.

Other objects, advantages and novel features of the present invention will become apparent from the following detailed description of the invention when considered in conjunction with the accompanying drawings.

SUMMARY OF THE INVENTION

These and other objects, features and advantages of the invention are accomplished by an integrated ultrasonic system and shockwave generating system wherein the ultrasonic system localizes the concretion and provides information to position the shockwave generating system. The shockwave generating system utilizes a reflector with a first and second focus with a spark gap located at the first focus and the reflector positioned so that the body concretion is located at the second focus. A flexible membrane encloses the fluid filled reflector and provides an interface between the patient and shockwave generator for the efficient transmission of the shock wave energy to the body concretion.

BRIEF DESCRIPTION OF THE DRAWINGS

The above and further objects and novel features of the invention will more fully appear from the following description when the same is read in connection with the accompanying drawings. It is to be understood, however, that the drawings are for the purpose of illustration only, and are not intended as a definition of the limits of the invention.

DESCRIPTION OF THE PREFERRED EMBODIMENT

Figure 1:
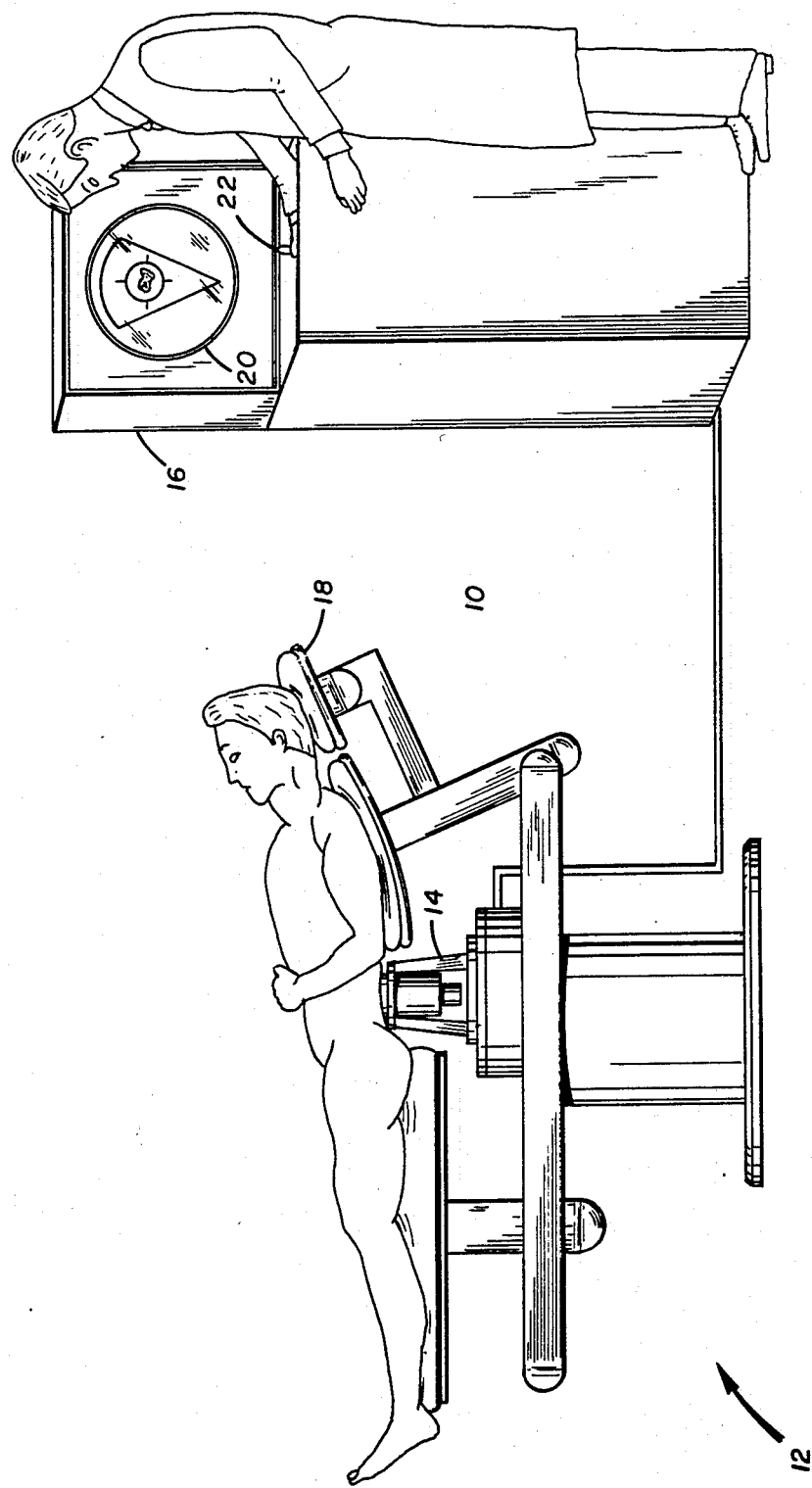
FIG. 1 is a pictorial representation of the present invention.

Referring now to the drawings, FIG. 1 is a pictorial representation of the system 10 as taught by the present invention. The system comprises three main sections; (1) the patient support system 12, (2) the shockwave-ultrasonic section 14 and (3) the ultrasonic display and control section 16. The patient support system 12 shown in the drawing is sectionalized table 18 with space allowed for access to the patient's kidney area by the shockwave-ultrasonic section 14. Another embodiment is to position the patient face down and suspend the shockwave-ultrasonic section 14 from an overhead system.

The shockwave-ultrasonic section 14 includes an ultrasonic transducer, to be described below, which provides ultrasonic position information of the concretion to ultrasonic display and control section 16. The ultrasonic display and control section 16 displays the position information on a visual display 20. A doctor or technician utilizes the position information to position the shockwave-ultrasonic section 14 in a position in which the shockwave will be most effective in fragmenting the concretion. The technician, as shown in FIG. 1, moves the shockwave-ultrasonic section 14 either manually or remotely using controls, such as a joystick 22, on the ultrasonic display and control section 16. When the shockwave-ultrasonic section 14 is positioned correctly the technician causes a shockwave to be generated from the ultrasonic display and control section 16.

Figure 2:
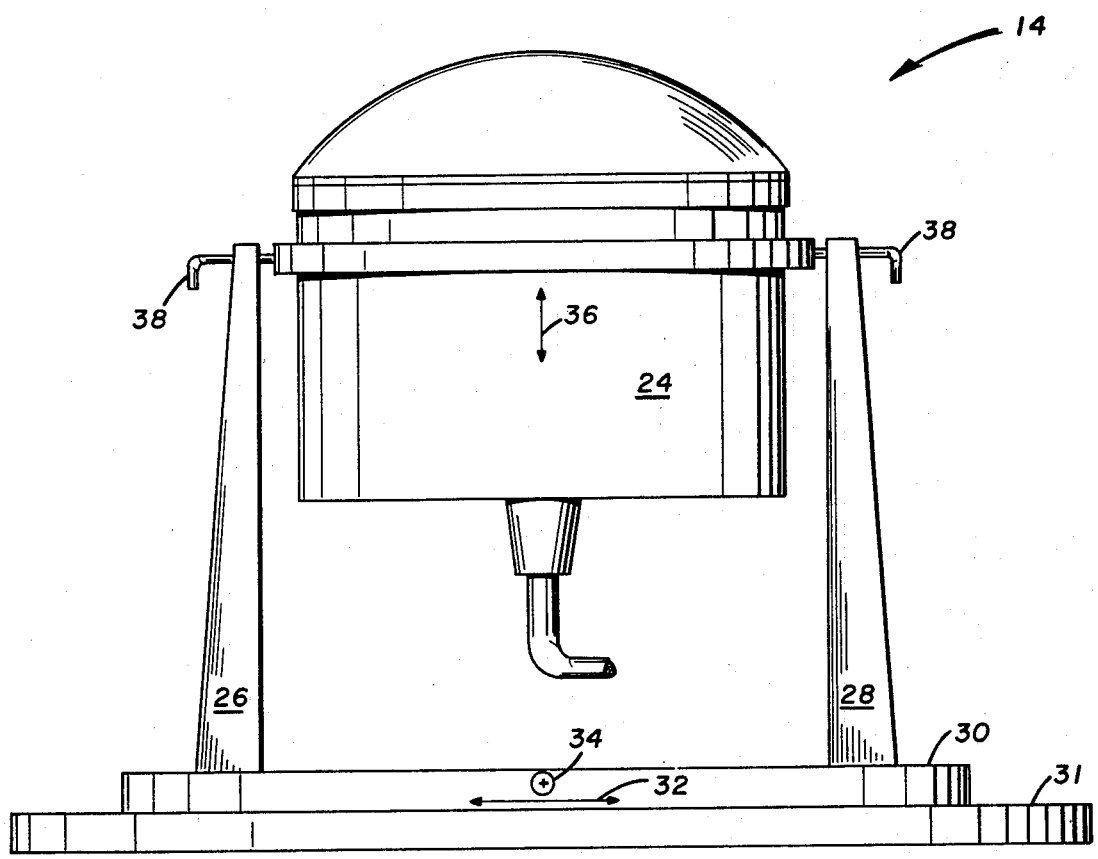
FIG. 2 is a pictorial representation of the shock wave-ultrasonic section.

FIG. 2 is a pictorial representation of the shockwave-ultrasonic section 14. The shockwave-ultrasonic section 14 comprises a main housing 24 and a support structure comprising legs 26, 28 mounted on a movable member 30 which is mounted on a stationary member 31. Member 30 is movable in a first direction represented by arrow 32 and in a second direction represented by the tail of arrow 34 shown going into the plane of the drawing. The main housing 24 is movable in a third direction represented by arrow 36. Movement in any of the directions may be remotely controlled from the ultrasonic display and control section 16 in which case motors mounted in shockwave-ultrasonic section 14 would move the main housing 24. Alternately, it is contemplated that movement in each or all three of the directions may be accomplished manually in which case handles, such as those shown at 38 could be loosened to allow the main housing 24 to be moved in the third direction, represented at 36, along tracks, not shown, in legs 26, 28, until the correct position is reached whereupon handles 38 are tightened to maintain the main housing 24 in position.

Figure 3:
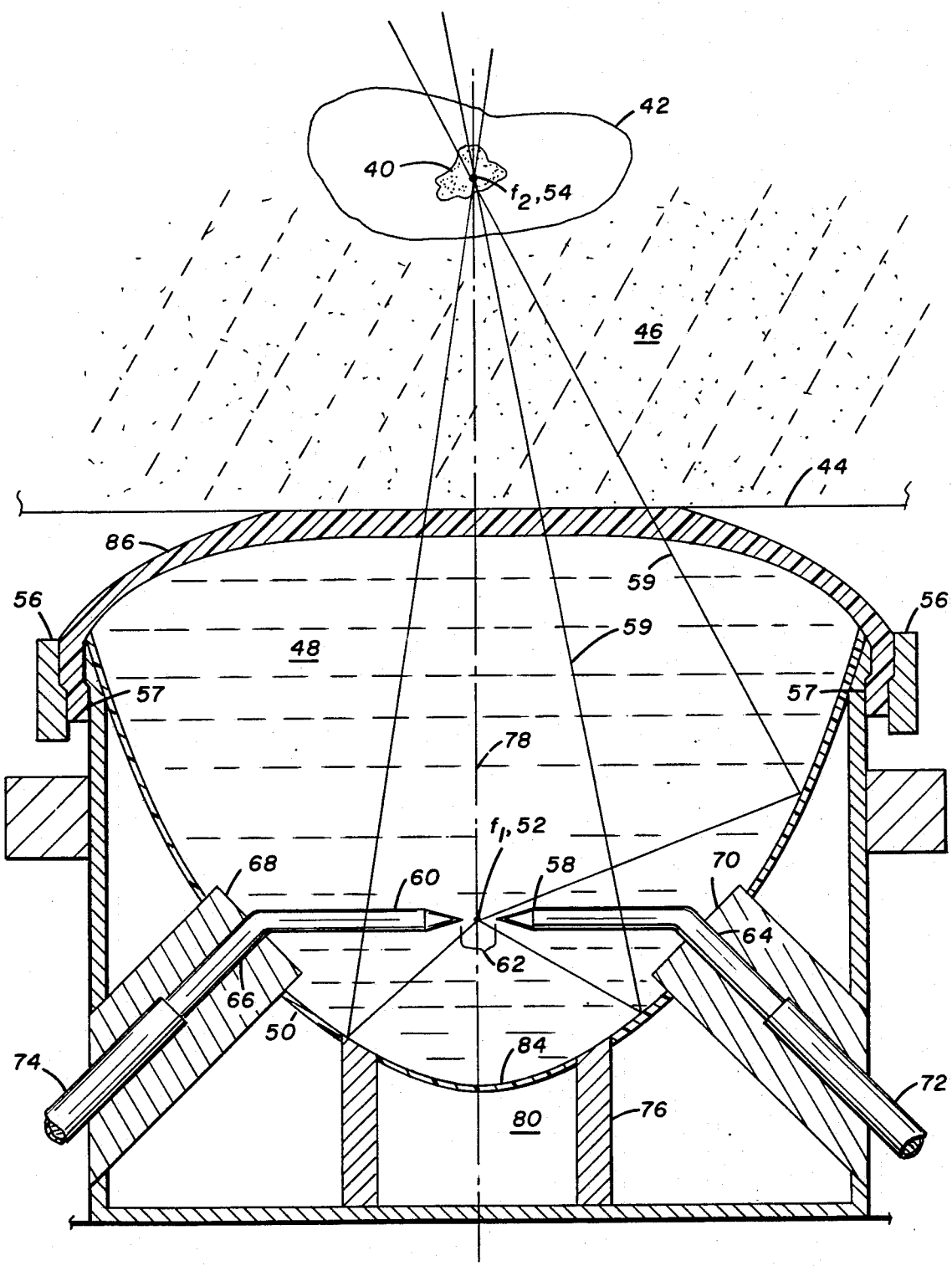
FIG. 3 is a cross sectional view of the main housing which includes the reflector and transducer.

FIG. 3 is a cross sectional view of main housing 24 and shows the positioning of the main housing 24 in relation to a concretion such as a kidney stone, represented at 40, in a human kidney, represented at 42. The patient's skin is represented at 44 and a portion of body tissue is represented at 46. The main housing 24 comprises a closed space 48 filled with a fluid with acoustical properties essentially similar to the acoustical properties of body tissue. Such a fluid could be water or a saline solution of water.

One portion of enclosed space 48 is bounded by a reflector surface 50 with a first focus $f_1$, represented at 52 and a second focus, $f_2$, represented at 54. The reflector surface of the preferred embodiment is described by an ellipsoid of revolution. The remaining portion of enclosed space 48 is bounded by a flexible membrane 86 which is held in place by a clamping ring 56 against an outer surface 57 of main housing 24. Electrodes 58, 60 with a spark gap, indicated at 62, centered around the first focus, $f_1$, 52 are throughput housing 24 at 64, 66 with suitable means for insulation 68, 70 from the structure of main housing 24. Leads 72, 74 lead to a high voltage supply, not shown. The spark gap 62 in the preferred embodiment is approximately 2-4 mm and the high voltage power supply provides a voltage across electrodes 58, 60 of approximately 10,000 volts. The generation of a spark between electrodes 58, 60 at the first focus $f_1$ causes a shockwave which is focused by the reflector surface 50 at the second focus $f_2$. Rays 59 indicate the focusing of the shockwave.

An ultrasonic transducer 76 is made integral with main housing 24 and is positioned at an end of the reflector surface 50. The ultrasonic transducer 76 is positioned so that an axis of the transducer is coincident with a line, indicated at 78, extending through the first and second focus, $f_1$ and $f_2$, of the ellipsoid of revolution. The transducer 76 is rotatable around the line 78 for at least an angle of ±90 degrees. The transducer 76 includes a radiating and detecting element 80 which radiates an acoustical signal and detects reflected portions of the acoustical signal. A flexible membrane 84 provides an interface between the radiating and detecting element 80 and the space 48.

Figure 4:
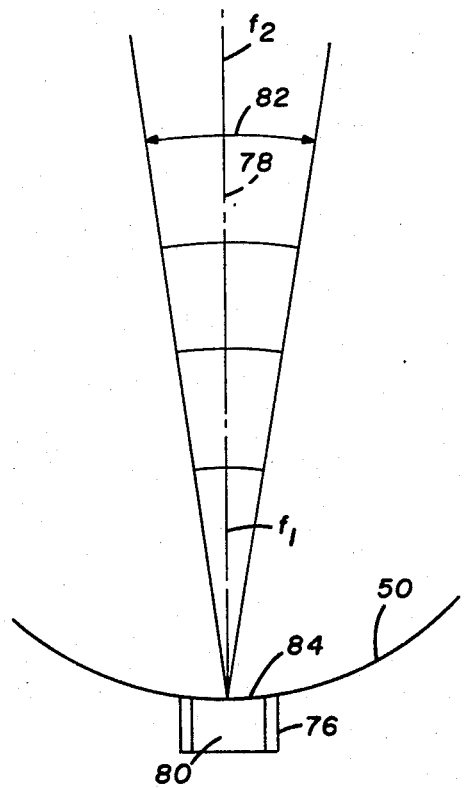
FIG. 4 is a pictorial representation of a portion of the main housing and a graphical representation of the radiated ultrasonic energy.

FIG. 4 is a pictorial representation of main housing 24 and transducer 76 and a graphical representation of the radiated ultrasonic radiation. The radiated acoustical signal is traversed in a plane within an angle 82 centered on line 78. As can be appreciated a rotation of transducer 76 causes a rotation of the plane in which the acoustical signal traverses. The detected reflected acoustical signal is displayed on visual display 20 on display and control section 16 (FIG. 1). The transducer 76 is caused to rotate by the doctor or technician until a body concretion is indicated on visual display 20. The doctor or technician moves the main housing in the first, second and third direction as discussed above until the concretion is located at the second focus of reflector 50. The third direction is perpendicular to both the first and second directions and is essentially perpendicular to the patient's body, i.e., movement in the third direction moves the main housing closer to or further away from the patient's body. Once the concretion is visually indicated as being at the second focal point $f_2$, a shock wave is initiated by the doctor and the process is repeated until the concretion is fragmented.

While the invention has been described with reference to the accompanying drawings, it is to be clearly understood that the invention is not to be limited to the particular details shown therein as obvious modifications may be made by those skilled in the art. The embodiments should only be construed within the scope of the following claims.

What we claim is:

1. A device for the noninvasive fragmentation of a concretion within a body of a patient, comprising:
   an ultrasonic transducer for locating said concretion;
   a reflector comprising a portion of an ellipsoid of revolution with an open end and a closed end, said transducer being attached to said closed end, said reflector having a first focus and a second focus, said transducer being positioned so that an axis of the transducer is coincident with a straight line extending through said first and second foci;
   means for positioning said reflector whereby said concretion is located at said second focus;
   means for generating a shock wave at said first focus; and
   means for acoustically coupling said shock wave from said first focus through a portion of said body to said second focus whereby said shock wave is concentrated at said concretion.

2. A device, as recited in claim 1, wherein said ultrasonic transducer is integral with said reflector.

3. A device, as recited in claim 2, wherein said ultrasonic transducer further comprises:
   means for radiating an acoustical signal from said transducer; and
   means for rotating said transducer around said axis from a first position to a second position wherein said second position is 90 degrees from said first position.

4. A device, as recited in claim 3, wherein said ultrasonic transducer further comprises means for traversing said acoustical signal within a predetermined angle whereby said acoustical signal traverses in a first plane when said transducer is in said first position and traverses in a second plane when said transducer is in said second position.

5. A device, as recited in claim 4, wherein said ultrasonic transducer further comprises:
   means for detecting reflected portions of said acoustical signal; and
   display means for displaying said reflected portions of said acoustical signal whereby said display means indicate location information of said concretion.

6. A device, as recited in claim 5, wherein said means for positioning comprise:
   means for moving said reflector in a first direction in response to said location information of said concretion;
   means for moving said reflector in a second direction in response to said location information of said concretion; and
   means for moving said reflector in a third direction in response to said location information of said concretion wherein said third direction is perpendicular to both said first direction and said second direction and movement in said third direction moves said reflector in a direction essentially perpendicular to said body.

7. A device, as recited in claim 6, wherein said means for generating a shock wave at said first focus comprise high voltage electrodes wherein a spark gap of said high voltage electrodes is centered at said first focus.

8. A device, as recited in claim 7, wherein said means for acoustically coupling said shock wave from said first focus through a portion of said body to said second focus comprises:
   a flexible membrane sealing said open end of said ellipsoid of revolution wherein said flexible membrane and said portion of an ellipsoid of revolution define a closed space; and
   a fluid medium filling said closed space wherein said fluid medium has essentially similar acoustic properties as said body.

9. A device, as recited in claim 8, wherein said fluid medium comprises water.

10. A device, as recited in claim 9, further comprising means for supporting said body.

11. A method for the noninvasive fragmentation of a concretion within a body of a patient, comprising the steps of:
    providing a reflector comprising a portion of an ellipsoid of revolution with an open end and a closed end and having first and second foci and an ultrasonic transducer having an axis coincident with a straight line passing through said first and second foci, said transducer attached to the closed end of said reflector;
    ultrasonically locating the concretion with said transducer;
    positioning said reflector so as to locate the concretion at the second focus;
    generating a shock wave at the first focus; and
    acoustically coupling the shock wave from the first focus through a portion of the body to the second focus whereby the shock wave is concentrated at the concretion.

12. A method, as recited in claim 11, wherein said step of ultrasonicly locating the concretion further comprises the steps of:
    radiating an acoustical signal;
    rotating the acoustical signal around an axis defined by a line extending through the first and second focus from a first position to a second position wherein the second position is 90 degrees from the first position; and
    traversing the acoustical signal within a predetermined angle whereby the acoustical signal traverses in a first plane when the acoustical signal is in the first position and traverses in a second plane when the acoustical signal is in the second position.

13. A method, as recited in claim 12, wherein said step of ultrasonicly locating the concretion further comprises the steps of:
    detecting reflected portions of the acoustical signal; and
    displaying the reflected portions of the acoustical signal on a visual display whereby location information of the concretion is indicated.

14. A method, as recited in claim 13, wherein the step of positioning a reflector further comprises the steps of:
    moving the reflector in a first direction in response to the location information of the concretion;
    moving the reflector in a second direction in response to the location information of the concretion; and
    moving the reflector in a third direction in response to the location information of the concretion wherein movement in the third direction moves the reflector in a direction essentially perpendicular to the body and wherein the third direction is perpendicular to both the first direction and the second direction.

* * * * *